US011445727B2

(12) United States Patent
Fabri et al.

(10) Patent No.: US 11,445,727 B2
(45) Date of Patent: *Sep. 20, 2022

(54) FUNGICIDAL COMBINATIONS

(71) Applicant: UPL LTD, Haldia (IN)

(72) Inventors: Carlos Eduardo Fabri, Sao Paulo -SP (BR); Rajju Devidas Shroff, Maharashtra (IN); Jaidev Rajnikant Shroff, Dubai (AE); Vikram Rajnikant Shroff, Dubai (AE)

(73) Assignee: UPL LTD, West Bengal (IN)

(*) Notice: Subject to any disclaimer, the term of this patent is extended or adjusted under 35 U.S.C. 154(b) by 0 days.

This patent is subject to a terminal disclaimer.

(21) Appl. No.: 16/347,283

(22) PCT Filed: Oct. 30, 2017

(86) PCT No.: PCT/IB2017/056710
§ 371 (c)(1),
(2) Date: May 3, 2019

(87) PCT Pub. No.: WO2018/083577
PCT Pub. Date: May 11, 2018

(65) Prior Publication Data
US 2019/0274307 A1    Sep. 12, 2019

(30) Foreign Application Priority Data
Nov. 4, 2016 (IN) .............................. 201631037704

(51) Int. Cl.
| A01N 47/14 | (2006.01) |
| A01N 37/36 | (2006.01) |
| A01N 43/16 | (2006.01) |
| A01N 43/40 | (2006.01) |
| A01N 43/54 | (2006.01) |
| A01N 43/56 | (2006.01) |
| A01N 43/60 | (2006.01) |
| A01N 43/653 | (2006.01) |
| A01N 45/02 | (2006.01) |

(52) U.S. Cl.
CPC ............. *A01N 47/14* (2013.01); *A01N 37/36* (2013.01); *A01N 43/16* (2013.01); *A01N 43/40* (2013.01); *A01N 43/54* (2013.01); *A01N 43/56* (2013.01); *A01N 43/60* (2013.01); *A01N 43/653* (2013.01); *A01N 45/02* (2013.01)

(58) Field of Classification Search
CPC ........ A01N 47/14; A01N 37/36; A01N 43/16; A01N 43/40; A01N 43/54; A01N 43/56; A01N 43/60; A01N 43/653; A01N 45/02
See application file for complete search history.

(56) References Cited

U.S. PATENT DOCUMENTS

| 10,362,782 | B2 * | 7/2019 | Oliveira | ............... | A01N 43/653 |
| 10,448,636 | B2 * | 10/2019 | Oliveira | ............... | A01N 43/40 |
| 10,537,101 | B2 * | 1/2020 | Oliveira | ............... | A01N 43/653 |
| 10,694,744 | B2 * | 6/2020 | Oliveira | ............... | A01N 25/00 |
| 10,694,745 | B2 * | 6/2020 | Oliveira | ............... | A01N 43/653 |
| 2008/0113979 | A1 | 5/2008 | Foor | | |
| 2009/0131462 | A1 | 5/2009 | Gewehr et al. | | |
| 2010/0216640 | A1 | 8/2010 | Tobler et al. | | |
| 2015/0181870 | A1 * | 7/2015 | Kemmitt | ............... | A01N 37/42 514/229.2 |
| 2016/0360751 | A1 * | 12/2016 | Oliveira | ............... | A01N 43/54 |
| 2020/0170251 | A1 * | 6/2020 | Hermenegildo de Oliveira | .......... | A01N 25/00 |
| 2021/0007355 | A1 | 1/2021 | Gongora et al. | | |
| 2021/0022343 | A1 | 1/2021 | Gongora et al. | | |
| 2021/0106006 | A1 | 4/2021 | Fabri et al. | | |
| 2021/0127679 | A1 | 5/2021 | Fabri et al. | | |
| 2021/0137119 | A1 | 5/2021 | Fabri et al. | | |
| 2022/0039388 | A1 | 2/2022 | Fabri et al. | | |

FOREIGN PATENT DOCUMENTS

| CA | 2969545 | A1 | 6/2016 |
| CN | 101222847 | A | 7/2008 |
| CN | 101677558 | A | 3/2010 |
| CN | 102258039 | A | 11/2011 |
| CN | 102835407 | A | 12/2012 |
| CN | 105744834 | A | 7/2016 |
| EP | 2783569 | * | 12/2014 |
| WO | 2006037632 | | 4/2006 |
| WO | 2006037634 | A1 | 4/2006 |
| WO | 2008095913 | A2 | 8/2008 |
| WO | 2013127818 | A1 | 9/2013 |
| WO | 2015079334 | A1 | 6/2015 |

OTHER PUBLICATIONS

Brent K. J. et al.; "Fungicide Resistance in Crop Pathogens: How Can It Be Managed?"; 2nd Revised Edition, Fungicide Resistance Action Committee, 2007, ISBN 90-72398-07-6; 60 pages.
International Search Report and Written Opinion; International Application No. PCT/IB2017/056710; International Filing Date Oct. 30, 2017; dated Jan. 12, 2018; 10 pages.
Lalancette, Norman, "New Fungicide for Apple Disease Control" Plant & Pest Advisory, Rutgers Cooperative Extension, Mar. 17, 2016, 2 pages.
Rosenberger, David; "Apple Scab Models & Suggestions for Scab Control in 2015"; 70th North Jersey Commercial Fruit Growers Meeting, Flemington, NJ, Mar. 4, 2015, 31 pages.
Rosenberger Presentation "Fire Blight and NEWA—How to Control Blight in 2015"; 70th North Jersey Commercial Fruit Growers Meeting; Mar. 4, 2015, Flemington, NJ; 43 pages.

* cited by examiner

*Primary Examiner* — Mina Haghighatian
(74) *Attorney, Agent, or Firm* — Cantor Colburn LLP

(57) ABSTRACT

A combination comprising a dithiocarbamate fungicide, a succinate dehydrogenase fungicide and at least one of ergosterol biosynthesis inhibitor fungicide or a quinone outside inhibitor fungicide.

10 Claims, No Drawings

FUNGICIDAL COMBINATIONS

CROSS REFERENCE TO RELATED APPLICATIONS

This application is a National Stage application of PCT/IB2017/056710, filed on Oct. 30, 2017, which claims the benefit of Indian Application No. 201631037704, filed on Nov. 4, 2016, both of which are incorporated by reference in their entirety herein.

TECHNICAL FIELD

The present invention relates to a combination of fungicides. More specifically, the present invention relates to fungicidal combinations comprising succinate dehydrogenase inhibitor fungicides for controlling a broad spectrum of fungal diseases.

BACKGROUND OF THE INVENTION

Fungicides are an integral and important tool yielded by farmers to control diseases, as well as to improve yields and quality of the crops. There are various fungicides that have been developed over the years with many desirable attributes such as specificity, systemicity, curative and eradicant action and high activity at low use rates.

Succinate dehydrogenase inhibitor (SDHI) fungicides are known in the art to be broad spectrum and have a high potency. Pyrazolecarboxamides are a group of active compounds within the SDHI family of fungicides that are known to be more potent than most other SDHI fungicides. These molecules specifically bind to the ubiquinone-binding site (Q-site) of the mitochondrial complex II, thereby inhibiting fungal respiration. These fungicides are known to control a broad spectrum of fungal diseases.

Various other classes of fungicides are also known in the art, such as Quinone outside inhibitors (QoIs), ergosterol-biosynthesis inhibitors, fungicides that act on multiple sites, fungicides that affect mitosis etc. These fungicides have been mixed with SDHI fungicides to achieve a broad spectrum of disease control.

WO2006037632 teaches combinations of SDHI fungicides with a second active compound. WO2013127818 teaches combinations of SDHI fungicides with various herbicides. WO2006037634 teaches methods of controlling fungi using a combination of SDHI fungicide with various fungicides. However, the prior art does not teach the use of ternary or higher combinations of SDHI fungicides.

Dithiocarbamate are known in the art as multi-site fungicides. These fungicides are used for broad-spectrum disease control in more than 70 crops. Mancozeb is especially important for controlling devastating and fast spreading diseases such as Phytophthora infestans, Venturia inaequalis etc. Dithiocarbamate fungicides, especially mancozeb, are particularly useful for disease control because of their broad spectrum of activity, high tolerance by crop plants, and general usefulness for controlling fungal plant diseases not controlled by active compounds that act on only a single target site in the fungus.

Mancozeb has been combined with various SDHI fungicides for disease control. There is a need in the art to improve on the disease spectrum provided by these combinations.

There is therefore a need in the art for combinations of SDHIs with a specific fungicide that helps improve spectrum. With crop tolerances decreasing, lower use rates being imposed and resistance being increasingly observed, there is a need for a combination of actives that allows for broader disease control spectrum that combines curative and preventive actives and has a lower dosage.

Therefore, embodiments of the present invention may ameliorate one or more of the above mentioned problems:

Therefore, embodiments of the present invention may provide combinations of fungicides that possess an enhanced efficacy over the individual fungicides used in isolation.

Another object of the present invention is to provide a fungicidal combination that causes an enhanced greening of the crops to which it is administered.

Another object of the present invention is to provide a fungicidal combination that causes late senescence to the crop to which it is applied thereby resulting into an increasing yield of the crop.

Yet another object of the present invention is to provide a fungicidal combination that results into reduced fungal disease incidence in the crops to which it is applied.

Another object of the present invention is to provide a fungicidal combination that achieves increased yield in the crops to which it is applied.

Some or all these and other objects of the invention are can be achieved by way of the invention described hereinafter.

SUMMARY OF THE INVENTION

Thus, an aspect of the present invention can provide a fungicidal combination comprising at least one succinate dehydrogenase inhibitor fungicide, at least one dithiocarbamate fungicide, and at least another fungicide.

Another aspect of the present invention can provide a fungicidal combination comprising at least one succinate dehydrogenase inhibitor fungicide, at least one dithiocarbamate fungicide and at least two other fungicides.

Another aspect of the present invention can provide synergistic compositions comprising at least one succinate dehydrogenase inhibitor fungicide, at least one dithiocarbamate fungicide, and at least one other fungicide.

Another aspect of the present invention can provide synergistic compositions comprising at least one succinate dehydrogenase inhibitor fungicide, at least one dithiocarbamate fungicide and at least two other fungicides.

DETAILED DESCRIPTION

The term 'disease control' as used herein denotes control and prevention of a disease. Controlling effects include all deviation from natural development, for example: killing, retardation, decrease of the fugal disease. The term 'plants' refers to all physical parts of a plant, including seeds, seedlings, saplings, roots, tubers, stems, stalks, foliage and fruits. The term locus: of a plant as used herein is intended to embrace the place on which the plants are growing, where the plant propagation materials of the plants are sown or where the plant propagation materials of the plants will be placed into the soil. The term plant propagation material: is understood to denote generative parts of a plant, such as seeds, vegetative material such as cuttings or tubers, roots, fruits, tubers, bulbs, rhizomes and parts of plants, germinated plants and young plants which are to be transplanted after germination or after emergence from the soil. These young plants may be protected before transplantation by a total or partial treatment by immersion. The term agriculturally acceptable amount of active: refers to an amount of an active that kills or inhibits the plant disease for which control is desired, in an amount not significantly toxic to the plant being treated.

Succinate dehydrogenase inhibitor (SDHI) fungicides play an important role in plant protection against many phytopathogenic fungi. These molecules specifically bind to the ubiquinone-binding site (Q-site) of the mitochondrial complex II, thereby inhibiting fungal respiration. Dithiocarbamate are multi-site contact fungicides. These molecules attack multiple sites within the fugal cells.

It has surprisingly been found that the addition of a dithiocarbamate fungicide to the combinations of succinate dehydrogenase inhibitors with at least another fungicide selected from an ergosterol biosynthesis inhibitors or Quinone outside inhibitors or a combination thereof, resulted in surprising and unexpected advantages. It was surprising that the addition of a dithiocarbamate fungicide to the combination of a succinate dehydrogenase inhibitor with at least another fungicide selected from an ergosterol biosynthesis inhibitors and/or Quinone outside inhibitors or a combination thereof resulted in an enhancement of the efficacy, and a surprising reduction in fungal disease incidence, seen only with the combination of succinate dehydrogenase inhibitors with at least another fungicide selected from an ergosterol biosynthesis inhibitors or Quinone outside inhibitors or a combination thereof. It has further been found that the addition of a dithiocarbamate fungicide to these combinations and application of these combinations during the flowering stage of the crop delayed the senescence in the crop to which they were applied, which led to better greening in the crop thereby increasing the level of photosynthesis occurring within the plant, thereby leading to a greater yield from the crop to which they were applied.

These surprising advantages of the combinations of the invention were not observed when the dithiocarbamate fungicide was not present in the combination. Therefore, these unexpected advantages of the combination of the present invention could be attributed to the inclusion of a dithiocarbamate fungicide to the combination of a succinate dehydrogenase inhibitor with at least another fungicide selected from an ergosterol biosynthesis inhibitors and/or Quinone outside inhibitors or a combination thereof.

Thus, in an aspect, the present invention provides a fungicidal combination comprising:
(a) at least one dithiocarbamate fungicide;
(b) at least one succinate dehydrogenase inhibitor fungicide; and
(c) at least another fungicide selected from an ergosterol biosynthesis inhibitors and/or Quinone outside inhibitors.

In an embodiment, the dithiocarbamate fungicide is selected from the group consisting of amobam, asomate, azithiram, carbamorph, cufraneb, cuprobam, disulfiram, ferbam, metam, nabam, tecoram, thiram, urbacide, ziram, dazomet, etem, milneb, mancopper, mancozeb, maneb, metiram, polycarbamate, propineb and zineb.

In an embodiment, the preferred dithiocarbamate fungicide is mancozeb.

In an embodiment, the succinate dehydrogenase inhibitor is selected from pyrazole carboxamide class of succinate dehydrogenase inhibitor fungicides. However, it should be understood that the choice of succinate dehydrogenase inhibitors is not understood to be limited to these pyrazole carboxamide fungicides alone.

In an embodiment, the pyrazole carboxamide class of succinate dehydrogenase inhibitor fungicide may be selected from benzovindiflupyr, bixafen, fluxapyroxad, furametpyr, isopyrazam, penflufen, penthiopyrad, and sedaxane.

Benzovindiflupyr has the chemical name N-[(1RS,4SR)-9-(dichloromethylene)-1,2,3,4-tetrahydro-1,4-methanonaphthalen-5-yl]-3-(difluoromethyl)-1-methylpyrazole-4-carboxamide and has the structure:

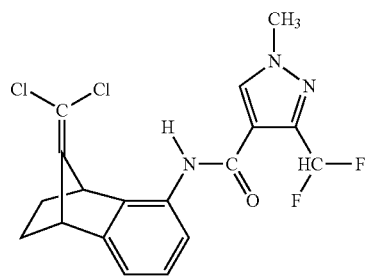 [SMILES: Cn1cc(C(=O)Nc2cccc3c2C2CCC3C2=C(Cl)Cl)c(C(F)F)n1]

Bixafen has the chemical name N-(3',4'-dichloro-5-fluorobiphenyl-2-yl)-3-(difluoromethyl)-1-methylpyrazole-4-carboxamide and the structure:

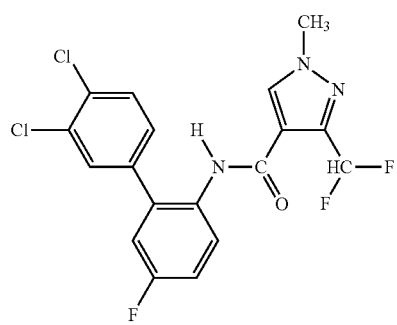 [SMILES: Cn1cc(C(=O)Nc2ccc(F)cc2-c2ccc(Cl)c(Cl)c2)c(C(F)F)n1]

Fluxapyroxad has the chemical name 3-(difluoromethyl)-1-methyl-N-(3',4',5'-trifluorobiphenyl-2-yl)pyrazole-4-carboxamide and has the structure:

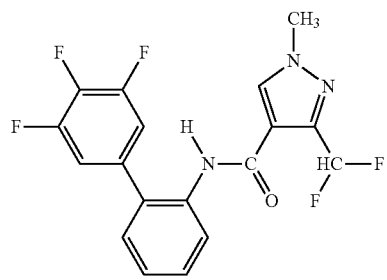 [SMILES: Cn1cc(C(=O)Nc2ccccc2-c2cc(F)c(F)c(F)c2)c(C(F)F)n1]

Furametpyr has the chemical name (RS)-5-chloro-N-(1,3-dihydro-1,1,3-trimethylisobenzofuran-4-yl)-1,3-dimethylpyrazole-4-carboxamide and has the structure:

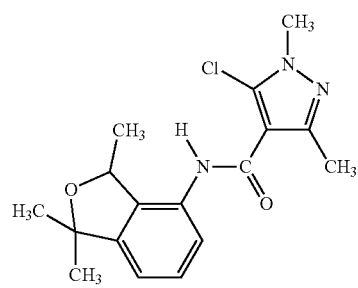

Isopyrazam is a mixture of 2 isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 aisomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide and its tautomer's have the structure:

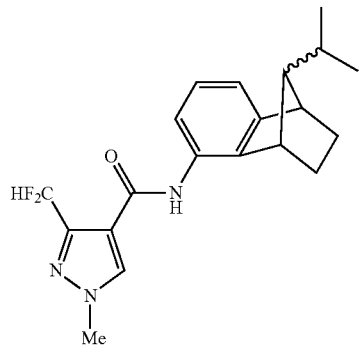

Penflufen has the chemical name N-[2-(1,3-dimethylbutyl)phenyl]-5-fluoro-1,3-dimethyl-1H-pyrazole-4-carboxamide, and has the following structure:

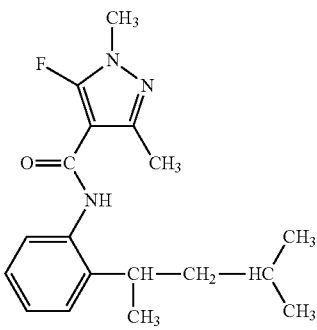 [SMILES: Cc1nn(C)c(F)c1C(=O)Nc1ccccc1C(C)CC(C)C]

Penthiopyrad has the chemical name (RS)—N-[2-(1,3-dimethylbutyl)-3-thienyl]-1-methyl-3-(trifluoromethyl)pyrazole-4-carboxamide, and has the following structure:

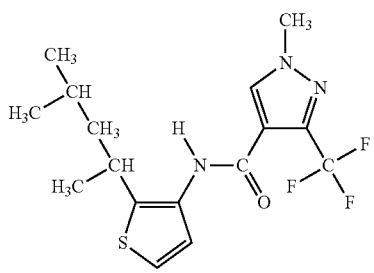 [SMILES: CC(C)CC(C)c1sccc1NC(=O)c1cn(C)nc1C(F)(F)F]

Sedaxane is a mixture of 2 cis-isomers 2'-[(1RS,2RS)-1,1'-bicycloprop-2-yl]-3-(difluoromethyl)-1-methylpyrazole-4-carboxanilide and 2 trans-isomers 2'-[(1RS,2SR)-1,1'-bicycloprop-2-yl]-3-(difluoromethyl)-1-methylpyrazole-4-carboxanilide, and its tautomer's have the structure:

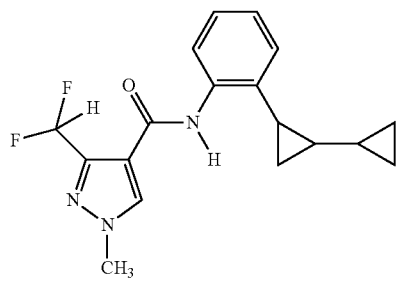 [SMILES: Cn1cc(C(=O)Nc2ccccc2C2CC2C2CC2)c(C(F)F)n1]

In an embodiment, the succinate dehydrogenase inhibitor fungicide may be selected from the group consisting of benodanil, flutolanil, mepronil, isofetamid, fluopyram, fenfuram, carboxin, oxycarboxin, thifluzamide, boscalid and IR9792.

In an embodiment, the third and/or fourth fungicides in the combinations of the present invention may be selected from ergosterol biosynthesis inhibitors, and/or Quinone outside (Qo) inhibitors or mixtures thereof.

Thus in an embodiment, the ergosterol biosynthesis inhibitors may be selected from the group consisting of azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, Ipconazole, metconazole, myclobutanil, penconazole, Propiconazole, simeconazole, tebuconazole, tetraconazole, triadimefon, triadimenol, triticonazole, prothioconazole, imazalil, oxpoconazole, pefurazoate, prochloraz, triflumizole, fenarimol, nuarimol, pyrifenox, pyrisoxazole, triforine and mixtures thereof.

In another embodiment, the ergosterol biosynthesis inhibitors may be selected from prothioconazole, tebuconazole, hexaconazole, cyroconazole or epoxiconazole.

In an embodiment, the third fungicide may be a Quinone outside (Qo) inhibitor fungicide selected from azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, dimoxystrobin, fenaminostrobin, metominostrobin, trifloxystrobin, famoxadone, fluoxastrobin, fenamidone, pyribencarb and mixtures thereof.

In an embodiment, the Quinone outside (Qo) inhibitor fungicide may be selected from azoxystrobin, picoxystrobin, kresoxim-methyl, pyraclostrobin and trifloxystrobin.

In an embodiment of the combinations of the present invention, the preferred succinate dehydrogenase inhibitor fungicide is isopyrazam.

In an embodiment, the combinations of the present invention include the following preferred combinations:

| S No. | I | II | III | IV |
|---|---|---|---|---|
| 1 | Mancozeb | Isopyrazam | Cyproconazole | — |
| 2 | Mancozeb | Isopyrazam | Difenoconazole | — |
| 3 | Mancozeb | Isopyrazam | Epoxiconazole | — |
| 4 | Mancozeb | Isopyrazam | Hexaconazole | — |
| 5 | Mancozeb | Isopyrazam | Tebuconazole | — |
| 6 | Mancozeb | Isopyrazam | Tetraconazole | — |
| 7 | Mancozeb | Isopyrazam | Prothioconazole | — |
| 8 | Mancozeb | Isopyrazam | — | Azoxystrobin |
| 9 | Mancozeb | Isopyrazam | — | Picoxystrobin |
| 10 | Mancozeb | Isopyrazam | — | Pyraclostrobin |
| 11 | Mancozeb | Isopyrazam | — | Kresoxim-methyl |

| S No. | I | II | III | IV |
|---|---|---|---|---|
| 12 | Mancozeb | Isopyrazam | — | Trifloxystrobin |
| 13 | Mancozeb | Isopyrazam | Cyproconazole | Azoxystrobin |
| 14 | Mancozeb | Isopyrazam | Cyproconazole | Picoxystrobin |
| 15 | Mancozeb | Isopyrazam | Cyproconazole | Pyraclostrobin |
| 16 | Mancozeb | Isopyrazam | Cyproconazole | Kresoxim-methyl |
| 17 | Mancozeb | Isopyrazam | Cyproconazole | Trifloxystrobin |
| 18 | Mancozeb | Isopyrazam | Difenoconazole | Azoxystrobin |
| 19 | Mancozeb | Isopyrazam | Difenoconazole | Picoxystrobin |
| 20 | Mancozeb | Isopyrazam | Difenoconazole | Pyraclostrobin |
| 21 | Mancozeb | Isopyrazam | Difenoconazole | Kresoxim-methyl |
| 22 | Mancozeb | Isopyrazam | Difenoconazole | Trifloxystrobin |
| 23 | Mancozeb | Isopyrazam | Epoxiconazole | Azoxystrobin |
| 24 | Mancozeb | Isopyrazam | Epoxiconazole | Picoxystrobin |
| 25 | Mancozeb | Isopyrazam | Epoxiconazole | Pyraclostrobin |
| 26 | Mancozeb | Isopyrazam | Epoxiconazole | Kresoxim-methyl |
| 27 | Mancozeb | Isopyrazam | Epoxiconazole | Trifloxystrobin |
| 28 | Mancozeb | Isopyrazam | Hexaconazole | Azoxystrobin |
| 29 | Mancozeb | Isopyrazam | Hexaconazole | Picoxystrobin |
| 30 | Mancozeb | Isopyrazam | Hexaconazole | Pyraclostrobin |
| 31 | Mancozeb | Isopyrazam | Hexaconazole | Kresoxim-methyl |
| 32 | Mancozeb | Isopyrazam | Hexaconazole | Trifloxystrobin |
| 33 | Mancozeb | Isopyrazam | Tebuconazole | Azoxystrobin |
| 34 | Mancozeb | Isopyrazam | Tebuconazole | Picoxystrobin |
| 35 | Mancozeb | Isopyrazam | Tebuconazole | Pyraclostrobin |
| 36 | Mancozeb | Isopyrazam | Tebuconazole | Kresoxim-methyl |
| 37 | Mancozeb | Isopyrazam | Tebuconazole | Trifloxystrobin |
| 38 | Mancozeb | Isopyrazam | Tetraconazole | Azoxystrobin |
| 39 | Mancozeb | Isopyrazam | Tetraconazole | Picoxystrobin |
| 40 | Mancozeb | Isopyrazam | Tetraconazole | Pyraclostrobin |
| 41 | Mancozeb | Isopyrazam | Tetraconazole | Kresoxim-methyl |
| 42 | Mancozeb | Isopyrazam | Tetraconazole | Trifloxystrobin |
| 43 | Mancozeb | Isopyrazam | Prothioconazole | Azoxystrobin |
| 44 | Mancozeb | Isopyrazam | Prothioconazole | Picoxystrobin |
| 45 | Mancozeb | Isopyrazam | Prothioconazole | Pyraclostrobin |
| 46 | Mancozeb | Isopyrazam | Prothioconazole | Kresoxim-methyl |
| 47 | Mancozeb | Isopyrazam | Prothioconazole | Trifloxystrobin |

In an embodiment of the combinations of the present invention, the preferred succinate dehydrogenase inhibitor fungicide is Benzovindiflupyr.

In an embodiment, the combinations of the present invention include the following preferred combinations:

| S No. | I | II | III | IV |
|---|---|---|---|---|
| 48 | Mancozeb | Benzovindiflupyr | Cyproconazole | — |
| 49 | Mancozeb | Benzovindiflupyr | Difenoconazole | — |
| 50 | Mancozeb | Benzovindiflupyr | Epoxiconazole | — |
| 51 | Mancozeb | Benzovindiflupyr | Hexaconazole | — |
| 52 | Mancozeb | Benzovindiflupyr | Tebuconazole | — |
| 53 | Mancozeb | Benzovindiflupyr | Tetraconazole | — |
| 54 | Mancozeb | Benzovindiflupyr | Prothioconazole | — |
| 55 | Mancozeb | Benzovindiflupyr | — | Azoxystrobin |
| 56 | Mancozeb | Benzovindiflupyr | — | Picoxystrobin |
| 57 | Mancozeb | Benzovindiflupyr | — | Pyraclostrobin |
| 58 | Mancozeb | Benzovindiflupyr | — | Kresoxim-methyl |
| 59 | Mancozeb | Benzovindiflupyr | — | Trifloxystrobin |
| 60 | Mancozeb | Benzovindiflupyr | Cyproconazole | Azoxystrobin |
| 61 | Mancozeb | Benzovindiflupyr | Cyproconazole | Picoxystrobin |
| 62 | Mancozeb | Benzovindiflupyr | Cyproconazole | Pyraclostrobin |
| 63 | Mancozeb | Benzovindiflupyr | Cyproconazole | Kresoxim-methyl |
| 64 | Mancozeb | Benzovindiflupyr | Cyproconazole | Trifloxystrobin |
| 65 | Mancozeb | Benzovindiflupyr | Difenoconazole | Azoxystrobin |
| 66 | Mancozeb | Benzovindiflupyr | Difenoconazole | Picoxystrobin |
| 67 | Mancozeb | Benzovindiflupyr | Difenoconazole | Pyraclostrobin |
| 68 | Mancozeb | Benzovindiflupyr | Difenoconazole | Kresoxim-methyl |
| 69 | Mancozeb | Benzovindiflupyr | Difenoconazole | Trifloxystrobin |
| 70 | Mancozeb | Benzovindiflupyr | Epoxiconazole | Azoxystrobin |
| 71 | Mancozeb | Benzovindiflupyr | Epoxiconazole | Picoxystrobin |
| 72 | Mancozeb | Benzovindiflupyr | Epoxiconazole | Pyraclostrobin |
| 73 | Mancozeb | Benzovindiflupyr | Epoxiconazole | Kresoxim-methyl |
| 74 | Mancozeb | Benzovindiflupyr | Epoxiconazole | Trifloxystrobin |
| 75 | Mancozeb | Benzovindiflupyr | Hexaconazole | Azoxystrobin |
| 76 | Mancozeb | Benzovindiflupyr | Hexaconazole | Picoxystrobin |
| 77 | Mancozeb | Benzovindiflupyr | Hexaconazole | Pyraclostrobin |
| 78 | Mancozeb | Benzovindiflupyr | Hexaconazole | Kresoxim-methyl |
| 79 | Mancozeb | Benzovindiflupyr | Hexaconazole | Trifloxystrobin |
| 80 | Mancozeb | Benzovindiflupyr | Tebuconazole | Azoxystrobin |
| 81 | Mancozeb | Benzovindiflupyr | Tebuconazole | Picoxystrobin |
| 82 | Mancozeb | Benzovindiflupyr | Tebuconazole | Pyraclostrobin |
| 83 | Mancozeb | Benzovindiflupyr | Tebuconazole | Kresoxim-methyl |
| 84 | Mancozeb | Benzovindiflupyr | Tebuconazole | Trifloxystrobin |
| 85 | Mancozeb | Benzovindiflupyr | Tetraconazole | Azoxystrobin |
| 86 | Mancozeb | Benzovindiflupyr | Tetraconazole | Picoxystrobin |
| 87 | Mancozeb | Benzovindiflupyr | Tetraconazole | Pyraclostrobin |
| 88 | Mancozeb | Benzovindiflupyr | Tetraconazole | Kresoxim-methyl |
| 89 | Mancozeb | Benzovindiflupyr | Tetraconazole | Trifloxystrobin |
| 90 | Mancozeb | Benzovindiflupyr | Prothioconazole | Azoxystrobin |
| 91 | Mancozeb | Benzovindiflupyr | Prothioconazole | Picoxystrobin |
| 92 | Mancozeb | Benzovindiflupyr | Prothioconazole | Pyraclostrobin |
| 93 | Mancozeb | Benzovindiflupyr | Prothioconazole | Kresoxim-methyl |
| 94 | Mancozeb | Benzovindiflupyr | Prothioconazole | Trifloxystrobin |

In an embodiment of the combinations of the present invention, the preferred succinate dehydrogenase inhibitor fungicide is Penthiopyrad.

In an embodiment, the combinations of the present invention include the following preferred combinations:

| S No. | I | II | III | IV |
|---|---|---|---|---|
| 95 | Mancozeb | Penthiopyrad | Cyproconazole | — |
| 96 | Mancozeb | Penthiopyrad | Difenoconazole | — |
| 97 | Mancozeb | Penthiopyrad | Epoxiconazole | — |
| 98 | Mancozeb | Penthiopyrad | Hexaconazole | — |
| 99 | Mancozeb | Penthiopyrad | Tebuconazole | — |
| 100 | Mancozeb | Penthiopyrad | Tetraconazole | — |
| 101 | Mancozeb | Penthiopyrad | Prothioconazole | — |
| 102 | Mancozeb | Penthiopyrad | — | Azoxystrobin |
| 103 | Mancozeb | Penthiopyrad | — | Picoxystrobin |
| 104 | Mancozeb | Penthiopyrad | — | Pyraclostrobin |
| 105 | Mancozeb | Penthiopyrad | — | Kresoxim-methyl |
| 106 | Mancozeb | Penthiopyrad | — | Trifloxystrobin |
| 107 | Mancozeb | Penthiopyrad | Cyproconazole | Azoxystrobin |
| 108 | Mancozeb | Penthiopyrad | Cyproconazole | Picoxystrobin |
| 109 | Mancozeb | Penthiopyrad | Cyproconazole | Pyraclostrobin |
| 110 | Mancozeb | Penthiopyrad | Cyproconazole | Kresoxim-methyl |
| 111 | Mancozeb | Penthiopyrad | Cyproconazole | Trifloxystrobin |
| 112 | Mancozeb | Penthiopyrad | Difenoconazole | Azoxystrobin |
| 113 | Mancozeb | Penthiopyrad | Difenoconazole | Picoxystrobin |
| 114 | Mancozeb | Penthiopyrad | Difenoconazole | Pyraclostrobin |
| 115 | Mancozeb | Penthiopyrad | Difenoconazole | Kresoxim-methyl |
| 116 | Mancozeb | Penthiopyrad | Difenoconazole | Trifloxystrobin |
| 117 | Mancozeb | Penthiopyrad | Epoxiconazole | Azoxystrobin |
| 118 | Mancozeb | Penthiopyrad | Epoxiconazole | Picoxystrobin |
| 119 | Mancozeb | Penthiopyrad | Epoxiconazole | Pyraclostrobin |
| 120 | Mancozeb | Penthiopyrad | Epoxiconazole | Kresoxim-methyl |
| 121 | Mancozeb | Penthiopyrad | Epoxiconazole | Trifloxystrobin |
| 122 | Mancozeb | Penthiopyrad | Hexaconazole | Azoxystrobin |

| S No. | I | II | III | IV |
|---|---|---|---|---|
| 123 | Mancozeb | Penthiopyrad | Hexaconazole | Picoxystrobin |
| 124 | Mancozeb | Penthiopyrad | Hexaconazole | Pyraclostrobin |
| 125 | Mancozeb | Penthiopyrad | Hexaconazole | Kresoxim-methyl |
| 126 | Mancozeb | Penthiopyrad | Hexaconazole | Trifloxystrobin |
| 127 | Mancozeb | Penthiopyrad | Tebuconazole | Azoxystrobin |
| 128 | Mancozeb | Penthiopyrad | Tebuconazole | Picoxystrobin |
| 129 | Mancozeb | Penthiopyrad | Tebuconazole | Pyraclostrobin |
| 130 | Mancozeb | Penthiopyrad | Tebuconazole | Kresoxim-methyl |
| 131 | Mancozeb | Penthiopyrad | Tebuconazole | Trifloxystrobin |
| 132 | Mancozeb | Penthiopyrad | Tetraconazole | Azoxystrobin |
| 133 | Mancozeb | Penthiopyrad | Tetraconazole | Picoxystrobin |
| 134 | Mancozeb | Penthiopyrad | Tetraconazole | Pyraclostrobin |
| 135 | Mancozeb | Penthiopyrad | Tetraconazole | Kresoxim-methyl |
| 136 | Mancozeb | Penthiopyrad | Tetraconazole | Trifloxystrobin |
| 137 | Mancozeb | Penthiopyrad | Prothioconazole | Azoxystrobin |
| 138 | Mancozeb | Penthiopyrad | Prothioconazole | Picoxystrobin |
| 139 | Mancozeb | Penthiopyrad | Prothioconazole | Pyraclostrobin |
| 140 | Mancozeb | Penthiopyrad | Prothioconazole | Kresoxim-methyl |
| 141 | Mancozeb | Penthiopyrad | Prothioconazole | Trifloxystrobin |

In an embodiment of the combinations of the present invention, the preferred succinate dehydrogenase inhibitor fungicide is boscalid.

In an embodiment, the combinations of the present invention include the following preferred combinations:

| S No. | I | II | III | IV |
|---|---|---|---|---|
| 142 | Mancozeb | Boscalid | Cyproconazole | — |
| 143 | Mancozeb | Boscalid | Difenoconazole | — |
| 144 | Mancozeb | Boscalid | Epoxiconazole | — |
| 145 | Mancozeb | Boscalid | Hexaconazole | — |
| 146 | Mancozeb | Boscalid | Tebuconazole | — |
| 147 | Mancozeb | Boscalid | Tetraconazole | — |
| 148 | Mancozeb | Boscalid | Prothioconazole | — |
| 149 | Mancozeb | Boscalid | — | Azoxystrobin |
| 150 | Mancozeb | Boscalid | — | Picoxystrobin |
| 151 | Mancozeb | Boscalid | — | Pyraclostrobin |
| 152 | Mancozeb | Boscalid | — | Kresoxim-methyl |
| 153 | Mancozeb | Boscalid | — | Trifloxystrobin |
| 154 | Mancozeb | Boscalid | Cyproconazole | Azoxystrobin |
| 155 | Mancozeb | Boscalid | Cyproconazole | Picoxystrobin |
| 156 | Mancozeb | Boscalid | Cyproconazole | Pyraclostrobin |
| 157 | Mancozeb | Boscalid | Cyproconazole | Kresoxim-methyl |
| 158 | Mancozeb | Boscalid | Cyproconazole | Trifloxystrobin |
| 159 | Mancozeb | Boscalid | Difenoconazole | Azoxystrobin |
| 160 | Mancozeb | Boscalid | Difenoconazole | Picoxystrobin |
| 161 | Mancozeb | Boscalid | Difenoconazole | Pyraclostrobin |
| 162 | Mancozeb | Boscalid | Difenoconazole | Kresoxim-methyl |
| 163 | Mancozeb | Boscalid | Difenoconazole | Trifloxystrobin |
| 164 | Mancozeb | Boscalid | Epoxiconazole | Azoxystrobin |
| 165 | Mancozeb | Boscalid | Epoxiconazole | Picoxystrobin |
| 166 | Mancozeb | Boscalid | Epoxiconazole | Pyraclostrobin |
| 167 | Mancozeb | Boscalid | Epoxiconazole | Kresoxim-methyl |
| 168 | Mancozeb | Boscalid | Epoxiconazole | Trifloxystrobin |
| 169 | Mancozeb | Boscalid | Hexaconazole | Azoxystrobin |
| 170 | Mancozeb | Boscalid | Hexaconazole | Picoxystrobin |
| 171 | Mancozeb | Boscalid | Hexaconazole | Pyraclostrobin |
| 172 | Mancozeb | Boscalid | Hexaconazole | Kresoxim-methyl |
| 173 | Mancozeb | Boscalid | Hexaconazole | Trifloxystrobin |
| 174 | Mancozeb | Boscalid | Tebuconazole | Azoxystrobin |
| 175 | Mancozeb | Boscalid | Tebuconazole | Picoxystrobin |
| 176 | Mancozeb | Boscalid | Tebuconazole | Pyraclostrobin |
| 177 | Mancozeb | Boscalid | Tebuconazole | Kresoxim-methyl |
| 178 | Mancozeb | Boscalid | Tebuconazole | Trifloxystrobin |
| 179 | Mancozeb | Boscalid | Tetraconazole | Azoxystrobin |
| 180 | Mancozeb | Boscalid | Tetraconazole | Picoxystrobin |
| 181 | Mancozeb | Boscalid | Tetraconazole | Pyraclostrobin |
| 182 | Mancozeb | Boscalid | Tetraconazole | Kresoxim-methyl |
| 183 | Mancozeb | Boscalid | Tetraconazole | Trifloxystrobin |
| 184 | Mancozeb | Boscalid | Prothioconazole | Azoxystrobin |
| 185 | Mancozeb | Boscalid | Prothioconazole | Picoxystrobin |
| 186 | Mancozeb | Boscalid | Prothioconazole | Pyraclostrobin |
| 187 | Mancozeb | Boscalid | Prothioconazole | Kresoxim-methyl |
| 188 | Mancozeb | Boscalid | Prothioconazole | Trifloxystrobin |

In an embodiment of the combinations of the present invention, the preferred succinate dehydrogenase inhibitor fungicide is IR9792. IR9792 is a SDHI fungicide, developed by Isagro, with the proposed common name fluindapyr.

In an embodiment, the combinations of the present invention include the following preferred combinations:

| S No. | I | II | III | IV |
|---|---|---|---|---|
| 189 | Mancozeb | IR9792 | Cyproconazole | — |
| 190 | Mancozeb | IR9792 | Difenoconazole | — |
| 191 | Mancozeb | IR9792 | Epoxiconazole | — |
| 192 | Mancozeb | IR9792 | Hexaconazole | — |
| 193 | Mancozeb | IR9792 | Tebuconazole | — |
| 194 | Mancozeb | IR9792 | Tetraconazole | — |
| 195 | Mancozeb | IR9792 | Prothioconazole | — |
| 196 | Mancozeb | IR9792 | — | Azoxystrobin |
| 197 | Mancozeb | IR9792 | — | Picoxystrobin |
| 198 | Mancozeb | IR9792 | — | Pyraclostrobin |
| 199 | Mancozeb | IR9792 | — | Kresoxim-methyl |
| 200 | Mancozeb | IR9792 | — | Trifloxystrobin |
| 201 | Mancozeb | IR9792 | Cyproconazole | Azoxystrobin |
| 202 | Mancozeb | IR9792 | Cyproconazole | Picoxystrobin |
| 203 | Mancozeb | IR9792 | Cyproconazole | Pyraclostrobin |
| 204 | Mancozeb | IR9792 | Cyproconazole | Kresoxim-methyl |
| 205 | Mancozeb | IR9792 | Cyproconazole | Trifloxystrobin |
| 206 | Mancozeb | IR9792 | Difenoconazole | Azoxystrobin |
| 207 | Mancozeb | IR9792 | Difenoconazole | Picoxystrobin |
| 208 | Mancozeb | IR9792 | Difenoconazole | Pyraclostrobin |
| 209 | Mancozeb | IR9792 | Difenoconazole | Kresoxim-methyl |
| 210 | Mancozeb | IR9792 | Difenoconazole | Trifloxystrobin |
| 211 | Mancozeb | IR9792 | Epoxiconazole | Azoxystrobin |
| 212 | Mancozeb | IR9792 | Epoxiconazole | Picoxystrobin |
| 213 | Mancozeb | IR9792 | Epoxiconazole | Pyraclostrobin |
| 214 | Mancozeb | IR9792 | Epoxiconazole | Kresoxim-methyl |
| 215 | Mancozeb | IR9792 | Epoxiconazole | Trifloxystrobin |
| 216 | Mancozeb | IR9792 | Hexaconazole | Azoxystrobin |
| 217 | Mancozeb | IR9792 | Hexaconazole | Picoxystrobin |
| 218 | Mancozeb | IR9792 | Hexaconazole | Pyraclostrobin |
| 219 | Mancozeb | IR9792 | Hexaconazole | Kresoxim-methyl |
| 220 | Mancozeb | IR9792 | Hexaconazole | Trifloxystrobin |
| 221 | Mancozeb | IR9792 | Tebuconazole | Azoxystrobin |
| 222 | Mancozeb | IR9792 | Tebuconazole | Picoxystrobin |
| 223 | Mancozeb | IR9792 | Tebuconazole | Pyraclostrobin |
| 224 | Mancozeb | IR9792 | Tebuconazole | Kresoxim-methyl |
| 225 | Mancozeb | IR9792 | Tebuconazole | Trifloxystrobin |
| 226 | Mancozeb | IR9792 | Tetraconazole | Azoxystrobin |
| 227 | Mancozeb | IR9792 | Tetraconazole | Picoxystrobin |
| 228 | Mancozeb | IR9792 | Tetraconazole | Pyraclostrobin |
| 229 | Mancozeb | IR9792 | Tetraconazole | Kresoxim-methyl |
| 230 | Mancozeb | IR9792 | Tetraconazole | Trifloxystrobin |
| 231 | Mancozeb | IR9792 | Prothioconazole | Azoxystrobin |
| 232 | Mancozeb | IR9792 | Prothioconazole | Picoxystrobin |

-continued

| S No. | I | II | III | IV |
|---|---|---|---|---|
| 233 | Mancozeb | IR9792 | Prothioconazole | Pyraclostrobin |
| 234 | Mancozeb | IR9792 | Prothioconazole | Kresoxim-methyl |
| 235 | Mancozeb | IR9792 | Prothioconazole | Trifloxystrobin |

In an embodiment of the combinations of the present invention, the preferred succinate dehydrogenase inhibitor fungicide is Bixafen.

In an embodiment, the combinations of the present invention include the following preferred combinations:

| S No. | I | II | III | IV |
|---|---|---|---|---|
| 236 | Mancozeb | Bixafen | Cyproconazole | — |
| 237 | Mancozeb | Bixafen | Difenoconazole | — |
| 238 | Mancozeb | Bixafen | Epoxiconazole | — |
| 239 | Mancozeb | Bixafen | Hexaconazole | — |
| 240 | Mancozeb | Bixafen | Tebuconazole | — |
| 241 | Mancozeb | Bixafen | Tetraconazole | — |
| 242 | Mancozeb | Bixafen | Prothioconazole | — |
| 243 | Mancozeb | Bixafen | — | Azoxystrobin |
| 244 | Mancozeb | Bixafen | — | Picoxystrobin |
| 245 | Mancozeb | Bixafen | — | Pyraclostrobin |
| 246 | Mancozeb | Bixafen | — | Kresoxim-methyl |
| 247 | Mancozeb | Bixafen | — | Trifloxystrobin |
| 248 | Mancozeb | Bixafen | Cyproconazole | Azoxystrobin |
| 249 | Mancozeb | Bixafen | Cyproconazole | Picoxystrobin |
| 250 | Mancozeb | Bixafen | Cyproconazole | Pyraclostrobin |
| 251 | Mancozeb | Bixafen | Cyproconazole | Kresoxim-methyl |
| 252 | Mancozeb | Bixafen | Cyproconazole | Trifloxystrobin |
| 253 | Mancozeb | Bixafen | Difenoconazole | Azoxystrobin |
| 254 | Mancozeb | Bixafen | Difenoconazole | Picoxystrobin |
| 255 | Mancozeb | Bixafen | Difenoconazole | Pyraclostrobin |
| 256 | Mancozeb | Bixafen | Difenoconazole | Kresoxim-methyl |
| 257 | Mancozeb | Bixafen | Difenoconazole | Trifloxystrobin |
| 258 | Mancozeb | Bixafen | Epoxiconazole | Azoxystrobin |
| 259 | Mancozeb | Bixafen | Epoxiconazole | Picoxystrobin |
| 260 | Mancozeb | Bixafen | Epoxiconazole | Pyraclostrobin |
| 261 | Mancozeb | Bixafen | Epoxiconazole | Kresoxim-methyl |
| 262 | Mancozeb | Bixafen | Epoxiconazole | Trifloxystrobin |
| 263 | Mancozeb | Bixafen | Hexaconazole | Azoxystrobin |
| 264 | Mancozeb | Bixafen | Hexaconazole | Picoxystrobin |
| 265 | Mancozeb | Bixafen | Hexaconazole | Pyraclostrobin |
| 266 | Mancozeb | Bixafen | Hexaconazole | Kresoxim-methyl |
| 267 | Mancozeb | Bixafen | Hexaconazole | Trifloxystrobin |
| 268 | Mancozeb | Bixafen | Tebuconazole | Azoxystrobin |
| 269 | Mancozeb | Bixafen | Tebuconazole | Picoxystrobin |
| 270 | Mancozeb | Bixafen | Tebuconazole | Pyraclostrobin |
| 271 | Mancozeb | Bixafen | Tebuconazole | Kresoxim-methyl |
| 272 | Mancozeb | Bixafen | Tebuconazole | Trifloxystrobin |
| 273 | Mancozeb | Bixafen | Tetraconazole | Azoxystrobin |
| 274 | Mancozeb | Bixafen | Tetraconazole | Picoxystrobin |
| 275 | Mancozeb | Bixafen | Tetraconazole | Pyraclostrobin |
| 276 | Mancozeb | Bixafen | Tetraconazole | Kresoxim-methyl |
| 277 | Mancozeb | Bixafen | Tetraconazole | Trifloxystrobin |
| 278 | Mancozeb | Bixafen | Prothioconazole | Azoxystrobin |
| 279 | Mancozeb | Bixafen | Prothioconazole | Picoxystrobin |
| 280 | Mancozeb | Bixafen | Prothioconazole | Pyraclostrobin |
| 281 | Mancozeb | Bixafen | Prothioconazole | Kresoxim-methyl |
| 282 | Mancozeb | Bixafen | Prothioconazole | Trifloxystrobin |

In an embodiment of the combinations of the present invention, the preferred succinate dehydrogenase inhibitor fungicide is Fluxapyroxad.

In an embodiment, the combinations of the present invention include the following preferred combinations:

| S No. | I | II | III | IV |
|---|---|---|---|---|
| 283 | Mancozeb | Fluxapyroxad | Cyproconazole | — |
| 284 | Mancozeb | Fluxapyroxad | Difenoconazole | — |
| 285 | Mancozeb | Fluxapyroxad | Epoxiconazole | — |
| 286 | Mancozeb | Fluxapyroxad | Hexaconazole | — |
| 287 | Mancozeb | Fluxapyroxad | Tebuconazole | — |
| 288 | Mancozeb | Fluxapyroxad | Tetraconazole | — |
| 289 | Mancozeb | Fluxapyroxad | Prothioconazole | — |
| 290 | Mancozeb | Fluxapyroxad | — | Azoxystrobin |
| 291 | Mancozeb | Fluxapyroxad | — | Picoxystrobin |
| 292 | Mancozeb | Fluxapyroxad | — | Pyraclostrobin |
| 293 | Mancozeb | Fluxapyroxad | — | Kresoxim-methyl |
| 294 | Mancozeb | Fluxapyroxad | — | Trifloxystrobin |
| 295 | Mancozeb | Fluxapyroxad | Cyproconazole | Azoxystrobin |
| 296 | Mancozeb | Fluxapyroxad | Cyproconazole | Picoxystrobin |
| 297 | Mancozeb | Fluxapyroxad | Cyproconazole | Pyraclostrobin |
| 298 | Mancozeb | Fluxapyroxad | Cyproconazole | Kresoxim-methyl |
| 299 | Mancozeb | Fluxapyroxad | Cyproconazole | Trifloxystrobin |
| 300 | Mancozeb | Fluxapyroxad | Difenoconazole | Azoxystrobin |
| 301 | Mancozeb | Fluxapyroxad | Difenoconazole | Picoxystrobin |
| 302 | Mancozeb | Fluxapyroxad | Difenoconazole | Pyraclostrobin |
| 303 | Mancozeb | Fluxapyroxad | Difenoconazole | Kresoxim-methyl |
| 304 | Mancozeb | Fluxapyroxad | Difenoconazole | Trifloxystrobin |
| 305 | Mancozeb | Fluxapyroxad | Epoxiconazole | Azoxystrobin |
| 306 | Mancozeb | Fluxapyroxad | Epoxiconazole | Picoxystrobin |
| 307 | Mancozeb | Fluxapyroxad | Epoxiconazole | Pyraclostrobin |
| 308 | Mancozeb | Fluxapyroxad | Epoxiconazole | Kresoxim-methyl |
| 309 | Mancozeb | Fluxapyroxad | Epoxiconazole | Trifloxystrobin |
| 310 | Mancozeb | Fluxapyroxad | Hexaconazole | Azoxystrobin |
| 311 | Mancozeb | Fluxapyroxad | Hexaconazole | Picoxystrobin |
| 312 | Mancozeb | Fluxapyroxad | Hexaconazole | Pyraclostrobin |
| 313 | Mancozeb | Fluxapyroxad | Hexaconazole | Kresoxim-methyl |
| 314 | Mancozeb | Fluxapyroxad | Hexaconazole | Trifloxystrobin |
| 315 | Mancozeb | Fluxapyroxad | Tebuconazole | Azoxystrobin |
| 316 | Mancozeb | Fluxapyroxad | Tebuconazole | Picoxystrobin |
| 317 | Mancozeb | Fluxapyroxad | Tebuconazole | Pyraclostrobin |
| 318 | Mancozeb | Fluxapyroxad | Tebuconazole | Kresoxim-methyl |
| 319 | Mancozeb | Fluxapyroxad | Tebuconazole | Trifloxystrobin |
| 320 | Mancozeb | Fluxapyroxad | Tetraconazole | Azoxystrobin |
| 321 | Mancozeb | Fluxapyroxad | Tetraconazole | Picoxystrobin |
| 322 | Mancozeb | Fluxapyroxad | Tetraconazole | Pyraclostrobin |
| 323 | Mancozeb | Fluxapyroxad | Tetraconazole | Kresoxim-methyl |
| 324 | Mancozeb | Fluxapyroxad | Tetraconazole | Trifloxystrobin |
| 325 | Mancozeb | Fluxapyroxad | Prothioconazole | Azoxystrobin |
| 326 | Mancozeb | Fluxapyroxad | Prothioconazole | Picoxystrobin |
| 327 | Mancozeb | Fluxapyroxad | Prothioconazole | Pyraclostrobin |
| 328 | Mancozeb | Fluxapyroxad | Prothioconazole | Kresoxim-methyl |
| 329 | Mancozeb | Fluxapyroxad | Prothioconazole | Trifloxystrobin |

In an embodiment of the combinations of the present invention, the preferred succinate dehydrogenase inhibitor fungicide is Furametpyr.

In an embodiment, the combinations of the present invention include the following preferred combinations:

| S No. | I | II | III | IV |
|---|---|---|---|---|
| 330 | Mancozeb | Furametpyr | Cyproconazole | — |
| 331 | Mancozeb | Furametpyr | Difenoconazole | — |
| 332 | Mancozeb | Furametpyr | Epoxiconazole | — |
| 333 | Mancozeb | Furametpyr | Hexaconazole | — |
| 334 | Mancozeb | Furametpyr | Tebuconazole | — |
| 335 | Mancozeb | Furametpyr | Tetraconazole | — |
| 336 | Mancozeb | Furametpyr | Prothioconazole | — |
| 337 | Mancozeb | Furametpyr | — | Azoxystrobin |
| 338 | Mancozeb | Furametpyr | — | Picoxystrobin |
| 339 | Mancozeb | Furametpyr | — | Pyraclostrobin |

| S No. | I | II | III | IV |
|---|---|---|---|---|
| 340 | Mancozeb | Furametpyr | — | Kresoxim-methyl |
| 341 | Mancozeb | Furametpyr | — | Trifloxystrobin |
| 342 | Mancozeb | Furametpyr | Cyproconazole | Azoxystrobin |
| 343 | Mancozeb | Furametpyr | Cyproconazole | Picoxystrobin |
| 344 | Mancozeb | Furametpyr | Cyproconazole | Pyraclostrobin |
| 345 | Mancozeb | Furametpyr | Cyproconazole | Kresoxim-methyl |
| 346 | Mancozeb | Furametpyr | Cyproconazole | Trifloxystrobin |
| 347 | Mancozeb | Furametpyr | Difenoconazole | Azoxystrobin |
| 348 | Mancozeb | Furametpyr | Difenoconazole | Picoxystrobin |
| 349 | Mancozeb | Furametpyr | Difenoconazole | Pyraclostrobin |
| 350 | Mancozeb | Furametpyr | Difenoconazole | Kresoxim-methyl |
| 351 | Mancozeb | Furametpyr | Difenoconazole | Trifloxystrobin |
| 352 | Mancozeb | Furametpyr | Epoxiconazole | Azoxystrobin |
| 353 | Mancozeb | Furametpyr | Epoxiconazole | Picoxystrobin |
| 354 | Mancozeb | Furametpyr | Epoxiconazole | Pyraclostrobin |
| 355 | Mancozeb | Furametpyr | Epoxiconazole | Kresoxim-methyl |
| 356 | Mancozeb | Furametpyr | Epoxiconazole | Trifloxystrobin |
| 357 | Mancozeb | Furametpyr | Hexaconazole | Azoxystrobin |
| 358 | Mancozeb | Furametpyr | Hexaconazole | Picoxystrobin |
| 359 | Mancozeb | Furametpyr | Hexaconazole | Pyraclostrobin |
| 360 | Mancozeb | Furametpyr | Hexaconazole | Kresoxim-methyl |
| 361 | Mancozeb | Furametpyr | Hexaconazole | Trifloxystrobin |
| 362 | Mancozeb | Furametpyr | Tebuconazole | Azoxystrobin |
| 363 | Mancozeb | Furametpyr | Tebuconazole | Picoxystrobin |
| 364 | Mancozeb | Furametpyr | Tebuconazole | Pyraclostrobin |
| 365 | Mancozeb | Furametpyr | Tebuconazole | Kresoxim-methyl |
| 366 | Mancozeb | Furametpyr | Tebuconazole | Trifloxystrobin |
| 367 | Mancozeb | Furametpyr | Tetraconazole | Azoxystrobin |
| 368 | Mancozeb | Furametpyr | Tetraconazole | Picoxystrobin |
| 369 | Mancozeb | Furametpyr | Tetraconazole | Pyraclostrobin |
| 370 | Mancozeb | Furametpyr | Tetraconazole | Kresoxim-methyl |
| 371 | Mancozeb | Furametpyr | Tetraconazole | Trifloxystrobin |
| 372 | Mancozeb | Furametpyr | Prothioconazole | Azoxystrobin |
| 273 | Mancozeb | Furametpyr | Prothioconazole | Picoxystrobin |
| 374 | Mancozeb | Furametpyr | Prothioconazole | Pyraclostrobin |
| 375 | Mancozeb | Furametpyr | Prothioconazole | Kresoxim-methyl |
| 376 | Mancozeb | Furametpyr | Prothioconazole | Trifloxystrobin |

In an embodiment of the combinations of the present invention, the preferred succinate dehydrogenase inhibitor fungicide is Penflufen.

In an embodiment, the combinations of the present invention include the following preferred combinations:

| S No. | I | II | III | IV |
|---|---|---|---|---|
| 377 | Mancozeb | Penflufen | Cyproconazole | — |
| 378 | Mancozeb | Penflufen | Difenoconazole | — |
| 379 | Mancozeb | Penflufen | Epoxiconazole | — |
| 380 | Mancozeb | Penflufen | Hexaconazole | — |
| 381 | Mancozeb | Penflufen | Tebuconazole | — |
| 382 | Mancozeb | Penflufen | Tetraconazole | — |
| 383 | Mancozeb | Penflufen | Prothioconazole | — |
| 384 | Mancozeb | Penflufen | — | Azoxystrobin |
| 385 | Mancozeb | Penflufen | — | Picoxystrobin |
| 386 | Mancozeb | Penflufen | — | Pyraclostrobin |
| 387 | Mancozeb | Penflufen | — | Kresoxim-methyl |
| 388 | Mancozeb | Penflufen | — | Trifloxystrobin |
| 389 | Mancozeb | Penflufen | Cyproconazole | Azoxystrobin |
| 390 | Mancozeb | Penflufen | Cyproconazole | Picoxystrobin |
| 391 | Mancozeb | Penflufen | Cyproconazole | Pyraclostrobin |
| 392 | Mancozeb | Penflufen | Cyproconazole | Kresoxim-methyl |
| 393 | Mancozeb | Penflufen | Cyproconazole | Trifloxystrobin |
| 394 | Mancozeb | Penflufen | Difenoconazole | Azoxystrobin |
| 395 | Mancozeb | Penflufen | Difenoconazole | Picoxystrobin |
| 396 | Mancozeb | Penflufen | Difenoconazole | Pyraclostrobin |
| 397 | Mancozeb | Penflufen | Difenoconazole | Kresoxim-methyl |
| 398 | Mancozeb | Penflufen | Difenoconazole | Trifloxystrobin |
| 399 | Mancozeb | Penflufen | Epoxiconazole | Azoxystrobin |
| 400 | Mancozeb | Penflufen | Epoxiconazole | Picoxystrobin |
| 401 | Mancozeb | Penflufen | Epoxiconazole | Pyraclostrobin |
| 402 | Mancozeb | Penflufen | Epoxiconazole | Kresoxim-methyl |
| 403 | Mancozeb | Penflufen | Epoxiconazole | Trifloxystrobin |
| 404 | Mancozeb | Penflufen | Hexaconazole | Azoxystrobin |
| 405 | Mancozeb | Penflufen | Hexaconazole | Picoxystrobin |
| 406 | Mancozeb | Penflufen | Hexaconazole | Pyraclostrobin |
| 407 | Mancozeb | Penflufen | Hexaconazole | Kresoxim-methyl |
| 408 | Mancozeb | Penflufen | Hexaconazole | Trifloxystrobin |
| 409 | Mancozeb | Penflufen | Tebuconazole | Azoxystrobin |
| 410 | Mancozeb | Penflufen | Tebuconazole | Picoxystrobin |
| 411 | Mancozeb | Penflufen | Tebuconazole | Pyraclostrobin |
| 412 | Mancozeb | Penflufen | Tebuconazole | Kresoxim-methyl |
| 413 | Mancozeb | Penflufen | Tebuconazole | Trifloxystrobin |
| 414 | Mancozeb | Penflufen | Tetraconazole | Azoxystrobin |
| 415 | Mancozeb | Penflufen | Tetraconazole | Picoxystrobin |
| 416 | Mancozeb | Penflufen | Tetraconazole | Pyraclostrobin |
| 417 | Mancozeb | Penflufen | Tetraconazole | Kresoxim-methyl |
| 418 | Mancozeb | Penflufen | Tetraconazole | Trifloxystrobin |
| 419 | Mancozeb | Penflufen | Prothioconazole | Azoxystrobin |
| 420 | Mancozeb | Penflufen | Prothioconazole | Picoxystrobin |
| 421 | Mancozeb | Penflufen | Prothioconazole | Pyraclostrobin |
| 422 | Mancozeb | Penflufen | Prothioconazole | Kresoxim-methyl |
| 423 | Mancozeb | Penflufen | Prothioconazole | Trifloxystrobin |

In an embodiment of the combinations of the present invention, the preferred succinate dehydrogenase inhibitor fungicide is Sedaxane.

In an embodiment, the combinations of the present invention include the following preferred combinations:

| S No. | I | II | III | IV |
|---|---|---|---|---|
| 424 | Mancozeb | Sedaxane | Cyproconazole | — |
| 425 | Mancozeb | Sedaxane | Difenoconazole | — |
| 426 | Mancozeb | Sedaxane | Epoxiconazole | — |
| 427 | Mancozeb | Sedaxane | Hexaconazole | — |
| 428 | Mancozeb | Sedaxane | Tebuconazole | — |
| 429 | Mancozeb | Sedaxane | Tetraconazole | — |
| 430 | Mancozeb | Sedaxane | Prothioconazole | — |
| 431 | Mancozeb | Sedaxane | — | Azoxystrobin |
| 432 | Mancozeb | Sedaxane | — | Picoxystrobin |
| 433 | Mancozeb | Sedaxane | — | Pyraclostrobin |
| 434 | Mancozeb | Sedaxane | — | Kresoxim-methyl |
| 435 | Mancozeb | Sedaxane | — | Trifloxystrobin |
| 436 | Mancozeb | Sedaxane | Cyproconazole | Azoxystrobin |
| 437 | Mancozeb | Sedaxane | Cyproconazole | Picoxystrobin |
| 438 | Mancozeb | Sedaxane | Cyproconazole | Pyraclostrobin |
| 439 | Mancozeb | Sedaxane | Cyproconazole | Kresoxim-methyl |
| 440 | Mancozeb | Sedaxane | Cyproconazole | Trifloxystrobin |
| 441 | Mancozeb | Sedaxane | Difenoconazole | Azoxystrobin |
| 442 | Mancozeb | Sedaxane | Difenoconazole | Picoxystrobin |
| 443 | Mancozeb | Sedaxane | Difenoconazole | Pyraclostrobin |
| 444 | Mancozeb | Sedaxane | Difenoconazole | Kresoxim-methyl |
| 445 | Mancozeb | Sedaxane | Difenoconazole | Trifloxystrobin |
| 446 | Mancozeb | Sedaxane | Epoxiconazole | Azoxystrobin |
| 447 | Mancozeb | Sedaxane | Epoxiconazole | Picoxystrobin |
| 448 | Mancozeb | Sedaxane | Epoxiconazole | Pyraclostrobin |
| 449 | Mancozeb | Sedaxane | Epoxiconazole | Kresoxim-methyl |

-continued

| S No. | I | II | III | IV |
|---|---|---|---|---|
| 450 | Mancozeb | Sedaxane | Epoxiconazole | Trifloxystrobin |
| 451 | Mancozeb | Sedaxane | Hexaconazole | Azoxystrobin |
| 452 | Mancozeb | Sedaxane | Hexaconazole | Picoxystrobin |
| 453 | Mancozeb | Sedaxane | Hexaconazole | Pyraclostrobin |
| 454 | Mancozeb | Sedaxane | Hexaconazole | Kresoxim-methyl |
| 455 | Mancozeb | Sedaxane | Hexaconazole | Trifloxystrobin |
| 456 | Mancozeb | Sedaxane | Tebuconazole | Azoxystrobin |
| 457 | Mancozeb | Sedaxane | Tebuconazole | Picoxystrobin |
| 458 | Mancozeb | Sedaxane | Tebuconazole | Pyraclostrobin |
| 459 | Mancozeb | Sedaxane | Tebuconazole | Kresoxim-methyl |
| 460 | Mancozeb | Sedaxane | Tebuconazole | Trifloxystrobin |
| 461 | Mancozeb | Sedaxane | Tetraconazole | Azoxystrobin |
| 462 | Mancozeb | Sedaxane | Tetraconazole | Picoxystrobin |
| 463 | Mancozeb | Sedaxane | Tetraconazole | Pyraclostrobin |
| 464 | Mancozeb | Sedaxane | Tetraconazole | Kresoxim-methyl |
| 465 | Mancozeb | Sedaxane | Tetraconazole | Trifloxystrobin |
| 466 | Mancozeb | Sedaxane | Prothioconazole | Azoxystrobin |
| 467 | Mancozeb | Sedaxane | Prothioconazole | Picoxystrobin |
| 468 | Mancozeb | Sedaxane | Prothioconazole | Pyraclostrobin |
| 469 | Mancozeb | Sedaxane | Prothioconazole | Kresoxim-methyl |
| 470 | Mancozeb | Sedaxane | Prothioconazole | Trifloxystrobin |

The combinations of the present invention may be formulated in the form of a composition.

In an embodiment, the present invention may provide a composition comprising:
(a) at least one succinate dehydrogenase inhibitor fungicide;
(b) at least one dithiocarbamate fungicide;
(c) at least one quinone outside inhibitor; and
(d) at least one agrochemically acceptable excipient.

In an embodiment, the present invention may provide a composition comprising:
(a) at least one succinate dehydrogenase inhibitor fungicide;
(b) at least one dithiocarbamate fungicide;
(c) at least one ergostrol biosynthesis inhibitor; and
(d) at least one agrochemically acceptable excipient.

In an embodiment, the present invention may provide a composition comprising:
(a) at least one succinate dehydrogenase inhibitor fungicide;
(b) at least one dithiocarbamate fungicide;
(c) at least one a quinone outside inhibitor;
(d) at least one ergostrol biosynthesis inhibitor; and
(e) at least one agrochemically acceptable excipient.

The amount of a composition according to the invention to be applied, will depend on various factors, such as the subject of the treatment, such as, for example plants, soil or seeds; the type of treatment, such as, for example spraying, dusting or seed dressing; the purpose of the treatment, such as, for example prophylactic or therapeutic disease control; in case of disease control the type of fungi to be controlled or the application time. This amount of the combinations of the present invention to be applied can be readily deduced by a skilled agronomist.

Thus in an embodiment, the present invention may provide compositions comprising:
at least one pyrazaole carboxamide selected from benzovindiflupyr, bixafen, fluxapyroxad, furametpyr, isopyrazam, penflufen, penthiopyrad, and sedaxane;
at least one quinone outside inhibitor, and/or at least one ergostrol biosynthesis inhibitor; and
at least one dithiocarbamate fungicide;
said fungicides being combined in agrochemically acceptable amounts.

In an embodiment, the total amount of succinate dehydrogenase inhibitor in the composition may typically be in the range of 0.1 to 99% by weight, preferably 0.2 to 90% by weight. The total amount of dithiocarbamate fungicide in the composition may be in the range of 0.1 to 99% by weight. The total amount of ergostrol biosynthesis inhibitor in the composition may be in the range of 0.1 to 99% by weight. The total amount of Quinone outside inhibitor in the composition may be in the range of 0.1 to 99% by weight.

In an embodiment, the constituent fungicides of the combination of the present invention may be admixed in ratio of (1-80):(1-80):(1-80) of the dithiocarbamate fungicide, succinate dehydrogenase inhibitor fungicide and the third fungicide respectively.

In an embodiment, the constituents of the composition of the present invention may be tank mixed and sprayed at the locus of the infection, or may be alternatively be mixed with surfactants and then sprayed.

In an embodiment, the constituents of the composition of the present invention may be used for foliar application, ground or applications to plant propagation materials.

In an embodiment, the compositions of the present invention may typically be produce by mixing the actives in the composition with an inert carrier, and adding surfactants and other adjuvants and carriers as needed and formulated into solid, or liquid formulations, including but not limited to wettable powders, granules, dusts, Soluble (liquid) concentrates, suspension concentrates, oil in water emulsion, water in oil emulsion, emulsifiable concentrates, capsule suspensions, ZC formulations, oil dispersions or other known formulation types. The composition may also be used for treatment of a plant propagation material such as seeds etc.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The compositions according to the present invention is effective for the following plant diseases:

Disease in rice: Blast (Magnaporthe grisea), Helminthosporium leaf spot (Cochliobolus miyabeanus), sheath blight (Rhizoctonia solani), and bakanae disease (Gibberella fujikuroi).

Diseases in wheat: powdery mildew (Erysiphe graminis), Fusariuin head blight (Fusarium graminearum, F. avenacerum, F. culmorum, Microdochium nivale), rust (Puccinia striiformis, P. graminis, P. recondita), pink snow mold (Micronectriella nivale), Typhula snow blight (Typhula sp.), loose smut (Ustilago tritici), bunt (Tilletia caries), eyespot (Pseudocercosporella herpotrichoides), leaf blotch (Mycosphaerella graminicola), glume blotch (Stagonospora nodorum), septoria, and yellow spot (Pyrenophora tritici-repentis).

Diseases of barley: powdery mildew (Erysiphe graminis), Fusarium head blight (Fusarium graminearum, F. avenacerum, F. culmorum, Microdochium nivale), rust (Puccinia striiformis, P. graminis, P. hordei), loose smut (Ustilago nuda), scald (Rhynchosporium secalis), net blotch (Pyrenophora teres), spot blotch (Cochliobolus sativus), leaf stripe (Pyrenophora graminea), and Rhizoctonia damping-off (Rhizoctonia solani).

Diseases in corn: smut (Ustilago maydis), brown spot (Cochliobolus heterostrophus), copper spot (Gloeocercospora sorghi), southern rust (Puccinia polysora), gray leaf spot (Cercospora zeae-maydis), white spot (Phaeosphaeria mydis and/or Pantoea ananatis) and Rhizoctonia damping-off (Rhizoctonia solani).

Diseases of citrus: melanose (Diaporthe citri), scab (Elsinoe fawcetti), penicillium rot (Penicillium digitatum, P. italicum), and brown rot (Phytophthora parasitica, Phytophthora citrophthora).

Diseases of apple: blossom blight (Monilinia mali), canker (Valsa ceratosperma), powdery mildew (Podosphaera leucotricha), Alternaria leaf spot (Alternaria alternata apple pathotype), scab (Venturia inaequalis), powdery mildew, bitter rot (Colletotrichum acutatum), crown rot (Phytophtora cactorum), blotch (Diplocarpon mali), and ring rot (Botryosphaeria berengeriana).

Diseases of pear: scab (Venturia nashicola, V. pirina), powdery mildew, black spot (Alternaria alternata Japanese pear pathotype), rust (Gymnosporangium haraeanum), and phytophthora fruit rot (Phytophtora cactorum).

Diseases of peach: brown rot (Monilinia fructicola), powdery mildew, scab (Cladosporium carpophilum), and phomopsis rot (Phomopsis sp.).

Diseases of grape: anthracnose (Elsinoe ampelina), ripe rot (Glomerella cingulata), powdery mildew (Uncinula necator), rust (Phakopsora ampelopsidis), black rot (Guignardia bidwellii), botrytis, and downy mildew (Plasmopara viticola).

Diseases of Japanese persimmon: anthracnose (Gloeosporium kaki), and leaf spot (Cercospora kaki, Mycosphaerella nawae).

Diseases of gourd: anthracnose (Colletotrichum lagenarium), powdery mildew (Sphaerotheca fuliginea), gummy stem blight (Mycosphaerella melonis), Fusarium wilt (Fusarium oxysporum), downy mildew (Pseudoperonospora cubensis), Phytophthora rot (Phytophthora sp.), and damping-off (Pythium sp.).

Diseases of tomato: early blight (Alternaria solani), leaf mold (Cladosporium fulvum), and late blight (Phytophthora infestans).

Diseases of eggplant: brown spot (Phomopsis vexans), and powdery mildew (Erysiphe cichoracearum) Diseases of cruciferous vegetables: Alternaria leaf spot (Alternaria japonica), white spot (Cercosporella brassicae), clubroot (Plasmodiophora brassicae), and downy mildew (Peronospora parasitica).

Diseases of onion: rust (Puccinia allii), and downy mildew (Peronospora destructor).

Diseases of soybean: purple seed stain (Cercospora kikuchii), sphaceloma scad (Elsinoe glycines), pod and stem blight (Diaporthe phaseolorum var. sojae), septoria brown spot (Septoria glycines), frogeye leaf spot (Cercospora sojina), rust (Phakopsora pachyrhizi), Yellow rust, brown stem rot (Phytophthora sojae), and Rhizoctonia damping-off (Rhizoctonia solani).

Diseases of kidney bean: anthracnose (Colletotrichum lindemthianum). Diseases of peanut: leaf spot (Cercospora personata), brown leaf spot (Cercospora arachidicola) and southern blight (Sclerotium rolfsii).

Diseases of garden pea: powdery mildew (Erysiphe pisi), and root rot (Fusarium solani f. sp. pisi).

Diseases of potato: early blight (Alternaria solani), late blight (Phytophthora infestans), pink rot (Phytophthora erythroseptica), and powdery scab (Spongospora subterranean f. sp. subterranea).

Diseases of strawberry: powdery mildew (Sphaerotheca humuli), and anthracnose (Glomerella cingulata).

Diseases of tea: net blister blight (Exobasidium reticulatum), white scab (Elsinoe leucospila), gray blight (Pestalotiopsis sp.), and anthracnose (Colletotrichum theaesinensis).

Diseases of tobacco: brown spot (Alternaria longipes), powdery mildew (Erysiphe cichoracearum), anthracnose (Colletotrichum tabacum), downy mildew (Peronospora tabacina), and black shank (Phytophthora nicotianae).

Diseases of rapeseed: sclerotinia rot (Sclerotinia sclerotiorum), and Rhizoctonia damping-off (Rhizoctonia solani). Diseases of cotton: Rhizoctonia damping-off (Rhizoctonia solani).

Diseases of sugar beat: Cercospora leaf spot (Cercospora beticola), leaf blight (Thanatephorus cucumeris), Root rot (Thanatephorus cucumeris), and Aphanomyces root rot (Aphanomyces cochlioides).

Diseases of rose: black spot (Diplocarpon rosae), powdery mildew (Sphaerotheca pannosa), and downy mildew (Peronospora sparsa). Diseases of chrysanthemum and asteraceous plants: downy mildew (Bremia lactucae), leaf blight (Septoria chrysanthemi-indici), and white rust (Puccinia horiana).

Diseases of various groups: diseases caused by Pythium spp. (Pythium aphanidermatum, Pythium debarianum, Pythium graminicola, Pythium irregulare, Pythium ultimum), gray mold. (Botrytis cinerea), and Sclerotinia rot (Sclerotinia sclerotiorum).

Disease of Japanese radish: Alternaria leaf spot (Alternaria brassicicola).

Diseases of turfgrass: dollar spot (Sclerotinia homeocarpa), and brown patch and large patch (Rhizoctonia solani).

Disease of banana: Black sigatoka (Mycosphaerella fijiensis), Yellow sigatoka (Mycosphaerella musicola).

Disease of sunflower: downy mildew (Plasmopara halstedii).

Seed diseases or diseases in the early stages of the growth of various plants caused by Aspergillus spp., Penicillium spp., Fusarium spp., Gibberella spp., Tricoderma spp., Thielaviopsis spp., Rhizopus spp., Mucor spp., Corticium spp., Phoma spp., Rhizoctonia spp. and Diplodia spp.

Viral diseases of various plants mediated by Polymixa spp. or Olpidium spp. and so on.

The compositions of the present invention can be used in agricultural lands such as fields, paddy fields, lawns and orchards or in non-agricultural lands. The present invention may be used to control diseases in agricultural lands for cultivating the plants without any phytotoxicity to the plant.

Examples of the crops on which the present compositions may be used include but are not limited to corn, rice, wheat, barley, rye, oat, sorghum, cotton, soybean, peanut, buckwheat, beet, rapeseed, sunflower, sugar cane, tobacco, etc.; vegetables: solanaceous vegetables such as eggplant, tomato, pimento, pepper, potato, etc., cucurbit vegetables such as cucumber, pumpkin, zucchini, water melon, melon, squash, etc., cruciferous vegetables such as radish, white turnip, horseradish, kohlrabi, Chinese cabbage, cabbage, leaf mustard, broccoli, cauliflower, etc., asteraceous vegetables such as burdock, crown daisy, artichoke, lettuce, etc, liliaceous vegetables such as green onion, onion, garlic, and asparagus, ammiaceous vegetables such as carrot, parsley, celery, parsnip, etc., chenopodiaceous vegetables such as spinach, Swiss chard, etc., lamiaceous vegetables such as Perilla frutescens, mint, basil, etc, strawberry, sweet potato, Dioscorea japonica, colocasia, etc., flowers, foliage plants, turf grasses, fruits: pome fruits such apple, pear, quince, etc, stone fleshy fruits such as peach, plum, nectarine, Prunus mume, cherry fruit, apricot, prune, etc., citrus fruits such as orange, lemon, rime, grapefruit, etc., nuts such as chestnuts, walnuts, hazelnuts, almond, pistachio, cashew nuts, macadamia nuts, etc. berries such as blueberry, cranberry, blackberry, raspberry, etc., grape, kaki fruit, olive, plum, banana, coffee, date palm, coconuts, etc., trees other than fruit trees; tea, mulberry, flowering plant, trees such as ash, birch, dogwood, Eucalyptus, Ginkgo biloba, lilac, maple, Quercus, poplar, Judas tree, Liquidambar formosana, plane tree, zelkova, Japanese arborvitae, fir wood, hemlock, juniper, Pinus, Picea, and Taxus cuspidate, etc.

In an embodiment, the constituent fungicides of the combination of the present invention may be admixed in ratio of (1-80):(1-80):(1-80):(1:80)

In an aspect, the present invention may provide methods of controlling fungal diseases comprising applying a combination comprising:
(a) at least one succinate dehydrogenase inhibitor fungicide;
(b) at least one quinone outside inhibitor and/or at least one ergostrol biosynthesis inhibitor; and
(c) at least one dithiocarbamate fungicide.

In an embodiment, the succinate dehydrogenase inhibitor fungicide, the quinone outside inhibitor fungicide, the ergosterol biosynthesis inhibitor fungicide, and the dithiocarbamate fungicide may be selected according to any of the preferred embodiments of the combinations described hereinabove.

The combinations of the present invention may be sold as a pre-mix composition or a kit of parts such that individual actives may be mixed before spraying. Alternatively, the kit of parts may contain succinate dehydrogenase inhibitor fungicide and the dithiocarbamate fungicide pre-mixed and the third active may be admixed with an adjuvant such that the two components may be tank mixed before spraying.

The composition of the present invention maybe applied simultaneously as a tank mix or a formulation or may be applied sequentially. The application may be made to the soil before emergence of the plants, either pre-planting or post-planting. The application may be made as a foliar spray at different timings during crop development, with either one or two applications early or late post-emergence.

The compositions according to the invention can be applied before or after infection of the useful plants or the propagation material thereof by the fungi.

As will be demonstrated in the examples, the addition of a dithiocarbamate fungicide to a combination of succinate dehydrogenase inhibitors which are combined with Quinone outside inhibitors and/or ergosterol biosynthesis inhibitors, greatly improved the disease control as well as improved yield and demonstrated a synergistic effect. The lower the mixture performance in the disease control, the greater the additional benefit of the mancozeb when added to the compositions of the present invention.

EXAMPLES

Studies were conducted to study the addition of dithiocarbamate fungicides to succinate dehydrogenase inhibitor fungicides and at least one other fungicide and the contribution of the dithiocarbamate to the efficacy of these mixtures. Experiments were conducted over a period of two years to study the effect of the addition of dithiocarbamates on the efficacy of succinate dehydrogenase inhibitors alone and when combined with a co-fungicide such as a Quinone outside inhibitors and/or ergosterol biosynthesis inhibitor fungicide. Doses tested were at rates of 1500 g/ha for Mancozeb, 150 ml/ha for the ergosterol biosynthesis inhibitor, 200 g/ha for the Quinone outside inhibitor, 1000 g/ha and 200 g/ha for succinate dehydrogenase inhibitor fungicides. The combinatios were tested for efficacy of disease control in soybean for the control of Asian soybean rust. The trials were carried out at various locations in India.

The test were conducted on soybean cultivar Monsoy 9144 RR. The commercially available individual active ingredients were used at the indicated dosages.

Table 1: Table 1 shows the efficacy of mancozeb when added to combinations containing succinate dehydrogenase inhibitor fungicides and ergosterol biosynthesis inhibitor.

| Treatment | Dose rates (ml/g/ha) | Mean percent disease control 2015/16 | Mean percent disease control 2016/17 |
|---|---|---|---|
| Prothioconazole + Benzovindiflupyr | 150 + 200 | 88.04 | 71.04 |
| Prothioconazole + Benzovindiflupyr + Mancozeb | 150 + 200 + 1500 | 95.07 | 95.07 |
| Prothioconazole + Isopyrazam | 150 + 1000 | 87.14 | 70.23 |
| Prothioconazole + Isopyrazam + Mancozeb | 150 + 1000 + 1500 | 93.4 | 93.07 |
| Prothioconazole + Penthoipyrad | 150 + 1000 | 83.33 | 68.15 |
| Prothioconazole + Penthiopyrad + Mancozeb | 150 + 1000 + 1500 | 93.07 | 92.18 |

Table 1 clearly demonstrates the increase in control when mancozeb is added to the combination of ergosterol biosynthesis inhibitors and succinate dehydrogenase inhibitor fungicides.

Table 2: Table 2 demonstrates effiacacy when mancozeb is added to combinations of succinate dehydrogenase inhibitor fungicides and quinone outside inhibitor fungicides and ergosterol biosynthesis inhibitors.

| Treatment | Dose rates (ml/g/ha) | Mean percent disease control | |
|---|---|---|---|
| | | 2015/16 | 2016/17 |
| Prothioconazole + Benzovindiflupyr + Azoxystrobin | 150 + 200 + 500 | 93.07 | 91.07 |
| Prothioconazole + Benzovindiflupyr + Azoxystrobin + Mancozeb | 150 + 200 + 500 + 1500 | 96.36 | 95.03 |

Table 2 clearly demonstrates the importance of adding mancozeb to the combination. The addition of mancozeb improved disease control.

It was thus found that the incorporation of mancozeb greatly increased efficacy and disease control of the succinate dehydrogenase inhibitor fungicide treatments when mixed with ergosterol biosynthesis inhibitors or quinone outside inhibitors. It was thus concluded that the addition of mancozeb enhanced the efficacy of the combination and surpsingly gave a synergistic effect. The addition of a dithiocarbamate increased disease control and improved yield of plants. The instant invention is more specifically explained by above examples. However, it should be understood that the scope of the present invention is not limited by the examples in any manner. It will be appreciated by any person skilled in this art that the present invention includes aforesaid examples and further can be modified and altered within the technical scope of the present invention.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A fungicidal combination consisting of benzovindiflupyr, mancozeb, and at least another fungicide selected from an ergosterol biosynthesis inhibitor fungicide, and a quinone outside inhibitor fungicide,
   wherein the ergosterol biosynthesis inhibitor is selected from azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, imazalil, oxpoconazole, pefurazoate, prochloraz, triflumizole, fenarimol, nuarimol, pyrifenox, pyrisoxazole, triforine, and mixtures thereof; and
   wherein the quinone outside inhibitor fungicide is selected from azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, dimoxystrobin, fenaminostrobin, metominostrobin, trifloxystrobin, famoxadone, fluoxastrobin, fenamidone, pyribencarb, and mixtures thereof.

2. A fungicidal combination consisting of benzovindiflupyr, mancozeb, an ergosterol biosynthesis inhibitor fungicide, and a quinone outside inhibitor fungicide,
   wherein the ergosterol biosynthesis inhibitor is selected from azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, imazalil, oxpoconazole, pefurazoate, prochloraz, triflumizole, fenarimol, nuarimol, pyrifenox, pyrisoxazole, triforine, and mixtures thereof; and
   wherein the quinone outside inhibitor fungicide is selected from azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, dimoxystrobin, fenaminostrobin, metominostrobin, trifloxystrobin, famoxadone, fluoxastrobin, fenamidone, pyribencarb, and mixtures thereof.

3. The combination as claimed in claim 1, wherein the at least another fungicide is cyproconazole, difenoconazole, epoxiconazole, hexaconazole, hexaconazole, tebuconazole, tetraconazole, prothioconazole, azoxystrobin, picoxystrobin, pyraclostrobin, kresoxim-methyl, trifloxystrobin, or a combination thereof.

4. The combination as claimed in claim 1, wherein the at least another fungicide is prothioconazole and/or azoxystrobin.

5. A composition consisting of:
   at least one agrochemically acceptable excipient; and
   a fungicidal combination of:
   (a) benzovindiflupyr;
   (b) mancozeb; and
   (c) at least one ergostrol biosynthesis inhibitor and/or at least one quinone outside inhibitor;
   wherein the ergosterol biosynthesis inhibitor is selected from azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, imazalil, oxpoconazole, pefurazoate, prochloraz, triflumizole, fenarimol, nuarimol, pyrifenox, pyrisoxazole, triforine, and mixtures thereof; and
   wherein the quinone outside inhibitor fungicide is selected from azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, dimoxystrobin, fenaminostrobin, metominostrobin, trifloxystrobin, famoxadone, fluoxastrobin, fenamidone, pyribencarb, and mixtures thereof.

6. The composition as claimed in claim 5, wherein the composition is formulated into wettable powders, granules, dusts, soluble (liquid) concentrates, suspension concentrates, oil in water emulsion, water in oil emulsion, emulsifiable concentrates, capsule suspensions, a combination of a suspension concentrate (SC) and a capsule suspension (CS), or oil dispersions.

7. The combination as claimed in claim 1, wherein the benzovindiflupyr and mancozeb are admixed in ratio of 1:80 to 80:1.

8. The composition as claimed in claim 5, wherein the total amount of benzovinidiflupyr in the composition is in the range of 0.1 to 99% by weight, the total amount of mancozeb in the composition is in the range of 0.1 to 99% by weight; the total amount of ergostrol biosynthesis inhibitor in the composition is in the range of 0.1 to 99% by weight; and the total amount of quinone outside inhibitor in the composition is in the range of 0.1 to 99% by weight.

9. A method of foliar application, consisting of applying the combination of claim 1 to the foliage of a plant.

10. A method of controlling fungal diseases in plants consisting of, applying to the locus of the plant a combination consisting of:
- (a) benzovindiflupyr;
- (b) at least one quinone outside inhibitor and/or at least one ergostrol biosynthesis inhibitor; and
- (c) mancozeb, wherein the ergosterol biosynthesis inhibitor is selected from azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, imazalil, oxpoconazole, pefurazoate, prochloraz, triflumizole, fenarimol, nuarimol, pyrifenox, pyrisoxazole, triforine, and mixtures thereof; and wherein the quinone outside inhibitor fungicide is selected from azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, dimoxystrobin, fenaminostrobin, metominostrobin, trifloxystrobin, famoxadone, fluoxastrobin, fenamidone, pyribencarb, and mixtures thereof.

\* \* \* \* \*